United States Patent
Hoffman

(10) Patent No.: US 10,300,077 B2
(45) Date of Patent: May 28, 2019

(54) COMPOSITIONS AND METHODS FOR TREATING DEMENTIA

(71) Applicant: Steven Hoffman, Mahwah, NJ (US)

(72) Inventor: Steven Hoffman, Mahwah, NJ (US)

(73) Assignee: Steven Hoffman, Mahwah, NJ (US)

( * ) Notice: Subject to any disclaimer, the term of this patent is extended or adjusted under 35 U.S.C. 154(b) by 0 days.

(21) Appl. No.: 15/699,364

(22) Filed: Sep. 8, 2017

(65) Prior Publication Data

US 2018/0071316 A1   Mar. 15, 2018

Related U.S. Application Data

(60) Provisional application No. 62/393,140, filed on Sep. 12, 2016, provisional application No. 62/507,531, filed on May 17, 2017.

(51) Int. Cl.

| | | |
|---|---|---|
| *A61K 48/00* | (2006.01) | |
| *A61K 31/575* | (2006.01) | |
| *A61K 31/352* | (2006.01) | |
| *A61K 31/567* | (2006.01) | |
| *A61K 45/06* | (2006.01) | |
| *A61K 31/565* | (2006.01) | |
| *A61K 31/616* | (2006.01) | |

(52) U.S. Cl.
CPC .......... *A61K 31/575* (2013.01); *A61K 31/352* (2013.01); *A61K 31/565* (2013.01); *A61K 31/567* (2013.01); *A61K 31/616* (2013.01); *A61K 45/06* (2013.01)

(58) Field of Classification Search
CPC .............................. A61K 48/00; A61K 31/575
USPC ................................................. 514/171, 456
See application file for complete search history.

(56) References Cited

U.S. PATENT DOCUMENTS

| | | |
|---|---|---|
| 5,733,926 A | 3/1998 | Gorbach |
| 5,952,374 A | 9/1999 | Clarkson, Jr. et al. |
| 2008/0113951 A1 | 5/2008 | El-Naggar et al. |
| 2009/0123571 A1 | 5/2009 | Meehan |

FOREIGN PATENT DOCUMENTS

| | | |
|---|---|---|
| CN | 102397550 | 5/2013 |
| EP | 1281324 | 7/2002 |
| EP | 2781214 | 3/2013 |
| JP | H03 161442 | 7/1991 |
| WO | WO 2014/158547 | 10/2014 |

OTHER PUBLICATIONS

Szekely et al., NSAID Use and Dementia Risk in the Cardiovascular Health Study: Role of APOE and NSAID Type; Neurology, 70(1), pp. 17-24, Jan. 2008.
Fillit et al., Observations in a Preliminary Open Trial of Estradiol Therapy for Senile Dementia-Alzheimer's Type; Psychoneuroendocrinology, vol. 11, No. 3, pp. 337-345, 1986.
Coon, Estrogen Replacement Therapy and Alzheimer's Disease, https://web.archive.org/web/20150922023351/https://www.macalester.edu/academics/psychology/whatap/ubnrp/estrogen/ERTAlzheimers.html; Sep. 22, 2015.
Vang et al., "The Unexpected Uses of Urso and Taurousodeoxycholic Acid in the Treatment of Non-Liver Diseases" Global Advances in Health and Medicine, vol. 3, No. 3, pp. 58-69, May 2014.
Siiteri, Review of Studies on Estrogen Biosynthesis in the Human, Cancer Research, 42, pp. 3269s-3273s, Aug. 1982.

*Primary Examiner* — Raymond J Henley, III
(74) *Attorney, Agent, or Firm* — BakerHostetler

(57) ABSTRACT

The present disclosure is directed to methods, compositions, and kits for treating dementia.

23 Claims, No Drawings

COMPOSITIONS AND METHODS FOR TREATING DEMENTIA

CROSS-REFERENCE TO RELATED APPLICATIONS

This application claims the benefit of U.S. Provisional Patent Application No. 62/393,140, filed Sep. 12, 2016 and U.S. Provisional Patent Application No. 62/507,531, filed May 17, 2017, both of which are incorporated herein by reference.

TECHNICAL FIELD

The present disclosure relates generally to compositions, kits, and methods for the treatment of dementia.

BACKGROUND

Dementia is not a specific disease, but a condition that is associated with a wide range of symptoms that, in turn, are associated with a decline in memory, among other brain functions. Dementia can affect the young, middle aged, and elderly, but it is generally more prevalent in adults over the age of 60. More than three million cases of dementia are diagnosed yearly in the United States alone.

It is believed that dementia results from damage to nerve cells in the brain, brain cell death, and/or neurodegenerative diseases. Some dementias are believed to be due to exogenous factors such as mediations, deficiencies, such as vitamin deficiencies, head injuries, strokes, brain tumors, prion diseases, and HIV infection. However, no single one reason why a patient develops dementia has been identified.

Dementia can affect different areas of the brain, thereby resulting in different symptoms. The most common symptom of dementia is memory loss, which may be short term or long term, and greatly affects quality of life for patients of all ages. Although dementia generally cannot be cured, there are medications and therapies that can delay halt or even delay the progression of symptoms.

What are needed are effective methods of treating dementia.

SUMMARY

The present disclosure is directed to methods of treating dementia in a patient, comprising administering to the patient an effective amount of an isoflavone, an estradiol, an estradiol derivative, an estradiol prodrug, a cholic acid agent, or a pharmaceutically acceptable salt thereof, or a combination of any of the foregoing. Kits and pharmaceutical compositions for use in these methods are also described.

Other aspects and embodiments of the invention will be readily apparent from the following detailed description of the invention.

DETAILED DESCRIPTION OF ILLUSTRATIVE EMBODIMENTS

The present subject matter may be understood more readily by reference to the following detailed description which forms a part of this disclosure. It is to be understood that this invention is not limited to the specific compositions, methods, conditions or parameters described and/or shown herein, and that the terminology used herein is for the purpose of describing particular embodiments by way of example only and is not intended to be limiting of the claimed invention.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

As employed above and throughout the disclosure, the following terms and abbreviations, unless otherwise indicated, shall be understood to have the following meanings.

In the present disclosure the singular forms "a," "an," and "the" include the plural reference, and reference to a particular numerical value includes at least that particular value, unless the context clearly indicates otherwise. Thus, for example, a reference to "a compound" is a reference to one or more of such compounds and equivalents thereof known to those skilled in the art, and so forth. The term "plurality", as used herein, means more than one. When a range of values is expressed, it includes the stated endpoints of the range. Similarly, when values are expressed as approximations, by use of the antecedent "about," it is understood that the particular value forms another embodiment. All ranges are inclusive and combinable.

As used herein, the terms "component," "composition," "composition of compounds," "compound," "drug," "pharmacologically active agent," "active agent," "therapeutic," "therapy," "treatment," or "medicament" are used interchangeably herein to refer to a compound or compounds or composition of matter which, when administered to a subject (human or animal) induces a desired pharmacological and/or physiologic effect by local and/or systemic action.

As used herein, the terms "treatment" or "therapy" (as well as different forms thereof) include preventative (e.g., prophylactic), curative, or palliative treatment. As used herein, the term "treating" includes alleviating or reducing at least one adverse or negative effect or symptom of dementia.

As employed above and throughout the disclosure the term "effective amount" refers to an amount effective, at dosages, and for periods of time necessary, to achieve the desired result with respect to the treatment of the relevant disorder, condition, symptom, or side effect. It will be appreciated that the effective amount of components of the present disclosure will vary from patient to patient not only with respect to the particular compound, component or composition selected, the route of administration, and the ability of the components to elicit a desired result in the individual, but also with respect to factors such as the disease state or severity of the condition to be alleviated, hormone levels, age, sex, weight of the individual, the state of being of the patient, and the severity of the pathological condition being treated, concurrent medication or special diets then being followed by the particular patient, and other factors which those skilled in the art will recognize, with the appropriate dosage being at the discretion of the attending physician. Dosage regimes may be adjusted to provide improved therapeutic response. An effective amount is also one in which any toxic or detrimental effects of the components are outweighed by the therapeutically beneficial effects.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

Within the present invention, the disclosed compounds may be prepared in the form of pharmaceutically acceptable salts. "Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein can be prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic compounds of the present disclosure may exist as zwitterions. All forms of the compounds, including free acid, free base and zwitterions, are contemplated to be within the scope of the present invention. It is well known in the art that compounds containing both amino and carboxy groups often exist in equilibrium with their zwitterionic forms. Thus, any of the compounds described herein that contain, for example, both amino and carboxy groups, also include reference to their corresponding zwitterions.

The term "administering" means either directly administering a compound or composition of the present invention, or administering a prodrug, derivative or analog which will form an equivalent amount of the active compound or substance within the body.

The terms "subject," "individual," and "patient" are used interchangeably herein, and refer to an animal, for example a human, to whom treatment, including prophylactic treatment, with the pharmaceutical composition according to the present disclosure, is provided.

The term "inhibitor" as used herein includes compounds that inhibit the expression or activity of a protein, polypeptide or enzyme and does not necessarily mean complete inhibition of expression and/or activity. Rather, the inhibition includes inhibition of the expression and/or activity of a protein, polypeptide or enzyme to an extent, and for a time, sufficient to produce the desired effect.

The present disclosure is directed to methods of treating dementia in a patient by administering to the patient an effective amount of a cholic acid agent, an estradiol, an estradiol derivative, an estradiol prodrug, or an isoflavone. According to the disclosure, these methods include the treatment of dementia per se, as well as methods of treating one or more of the symptoms of dementia. As understood by those skilled in the art, the term "dementia" as used herein refers to a condition resulting from damage to the brain. In some embodiments, the dementia results from one or more conditions including, without limitation, Alzheimer's disease, vascular dementia, dementia with lewy bodies, mixed dementia, Parkinson's disease, frontotemporal dementia, Creutzfeldt Jakob disease, normal pressure hydrocephalus, Huntington's disease, or Wernick Korsakoff syndrome. In some embodiments, the patient has more than condition.

Also provided are methods for reducing the likelihood that a patient to whom a non-steroidal anti-inflammatory drug has been administered will develop dementia. Such methods comprise administering to the patient an effective amount of an isoflavone, an estradiol, an estradiol derivative, an estradiol prodrug, a cholic acid agent, or a pharmaceutically acceptable salt thereof, or a combination of any of the foregoing.

As those skilled in the art will readily appreciate, the symptoms of dementia are numerous and may vary from patient to patient. The symptoms may be physical, cognitive, psychological, or any combinations thereof. The symptoms may be mild, moderate or severe and/or may worsen over time. Cognitive changes associated with dementia include, without limitation, one or more of memory loss (short and long term), difficulty communicating or finding words, loss of function (difficulty reasoning or problem-solving, handling complex tasks, planning and organizing), difficulty with coordination and motor functions, confusion, inability to recognize sarcasm, repetitive behavior, difficulty coping with change, and disorientation. Psychological changes include, without limitation, one or more of a personality or mood change, apathy, depression, anxiety, inappropriate behavior, paranoia, agitation, hallucinations, or a reduction or loss of inhibitions. Physical symptoms include stroke-like symptoms such as muscle weakness or paralysis, drowsiness, becoming slower in physical movements or having difficulties moving, language problems such as not speaking, speaking less than normal, or difficulties in finding the right words, or incontinence.

Common symptoms of dementia include memory loss (short and long term), confusion, difficulty communicating or finding words, inability to recognize sarcasm, mood changes, loss of function, apathy, repetitive behavior, difficulty coping with change, and, becoming slower in physical movements or having difficulties moving, and any combination of these symptoms. In preferred embodiments, the methods of the disclosure are used to treat memory loss (short and long term) symptoms of dementia. In some embodiments, the methods of the disclosure are used to treat confusion symptoms of dementia. In other embodiments, the methods of the disclosure are used to treat difficulty communicating or finding words of dementia. In other embodiments, the methods of the disclosure are used to treat the inability to recognize sarcasm symptoms of dementia. In other embodiments, the methods of the disclosure are used to treat mood changes symptoms of dementia. In other embodiments, the methods of the disclosure are used to treat loss of function symptoms of dementia. In other embodiments, the methods of the disclosure are used to treat apathy symptoms of dementia. In other embodiments, the methods of the disclosure are used to treat repetitive behavior symptoms of dementia. In other embodiments, the methods of the disclosure are used to treat difficulty coping with change symptoms of dementia. In other embodiments, the methods of the disclosure are used to treat becoming slower in physical movements or having difficulties moving symptoms of dementia.

Other aspects of the disclosure are directed to methods of treating dementia in a patient by administering to the patient an effective amount of a cholic acid agent, an estradiol, an estradiol derivative, an estradiol prodrug, or an isoflavone.

As used herein a "cholic acid agent" is a compound that alters (i.e., elevates or decreases) circulating levels of bile acids or bile salts in a patient by, for example, downregulating cholesterol-7-α-hydroxylase. Preferred cholic agents are those that have the general structure of cholic acid:

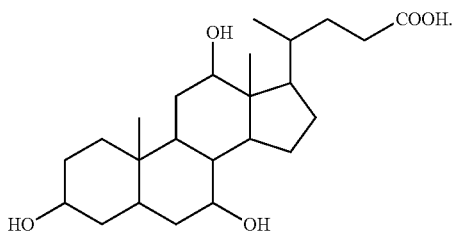 [SMILES: CC(CCC(=O)O)C1CCC2C3C(O)CC4CC(O)CCC4(C)C3CC(O)C12C]

In some embodiments, the cholic acid agent is 3α,7α,12α-trihydroxy-5β-cholan-24-oic acid:

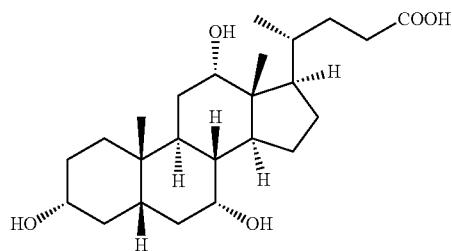

In other embodiments, the cholic acid agent or pharmaceutically acceptable salt thereof is, for example, ursodeoxycholic acid, cholic acid, chenodeoxycholic acid (also referred to as chenocholic acid), tauroursodeoxycholic acid (TUDCA), taurochenodeoxycholic acid, lithocholic acid, taurocholic acid, glycocholic acid, deoxycholic acid, or glycochenodeoxycholic acid, as well as combinations of the foregoing. In other embodiments, the cholic acid agent is cholic acid or chenodeoxycholic acid. In further embodiments, the cholic acid agent is cholic acid. One or any combination of cholic acid agents can be used in the methods of the disclosure.

As used herein, the terms "estradiol" and "estrogen" are interchangeable and refer to a compound having the following general backbone:

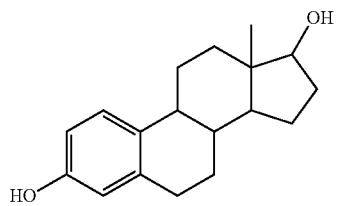 [SMILES: CC12CCC3c4ccc(O)cc4CCC3C1CCC2O]

In some embodiments, the estradiol is 17β-estradiol which has the following structure:

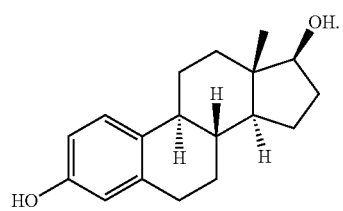

As used herein, the term "estradiol derivative" refers to a compound having the following general estradiol structure, wherein one or more available carbon atoms of the general estradiol backbone is substituted with a moiety aside from hydrogen. In some embodiments, the carbon atom at the 1-, 2-, 4-, 6-, 7-, 8-, 9-, 11-, 12-, 14-, 15-, 16-, or 17-position is substituted. In other embodiments, the carbon atom at the 1-, 2-, 4-, 6-, 7-, 11-, 12-, 15-, 16-, or 17-position is substituted. In further embodiments, the carbon atom at the 17-position is substituted.

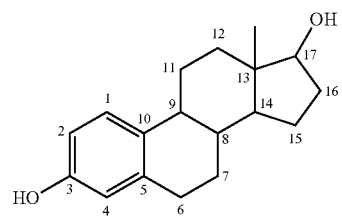 [SMILES: CC12CCC3c4ccc(O)cc4CCC3C1CCC2O]

In further embodiments, one or more carbon atom is substituted with one or two $C_{1-6}$alkyl, $C_{2-6}$alkenyl, or $C_{2-6}$alkynyl, as permitted by the valency of the carbon atom. In other embodiments, one or more carbon atom is substituted with $C_{1-6}$alkyl, such as methyl, ethyl, propyl, butyl, pentyl, or hexyl. In other embodiments, one or more carbon atom is substituted with $C_{2-6}$ alkenyl, such as ethenyl, propenyl, butenyl, pentenyl, or hexenyl. In other embodiments, one or more carbon atom is substituted with $C_{2-6}$ alkynyl, such as ethynyl, propynyl, butynyl, pentynyl, or hexynyl. Preferably, one or more carbon atom is substituted with ethynyl. An exemplary estradiol derivative is ethinyl estradiol:

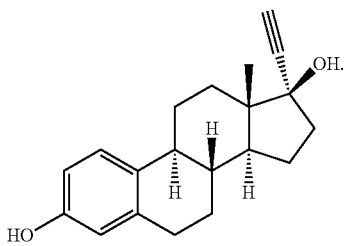

As used herein, the term "estradiol prodrug" refers to a chemical compound that converts in vivo to an estradiol when administered to a mammal. For example, the human body may metabolize the estradiol prodrug to an estradiol through the activity of, for example, an aromatase. In some embodiments, the estradiol prodrug contains the estradiol backbone discussed above, but instead contains a substituent bound to the oxygen atom of the OH group at the 3-position, the OH group at the 17-position, or the both OH groups as follows:

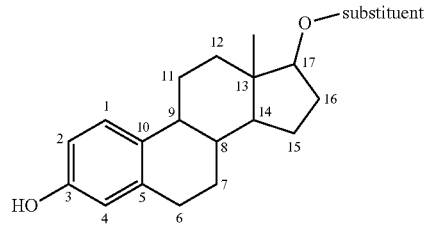

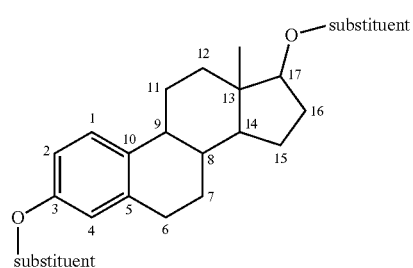

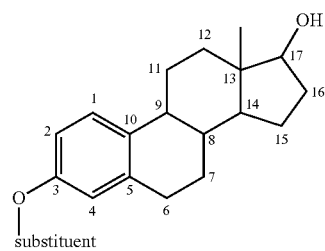

Representative substituents include a glucuronide

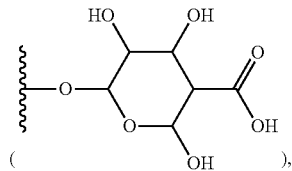 [SMILES: *OC1OC(O)C(C(=O)O)C(O)C1O]

acyl (—C(O)R), ester (—C(O)OR), carbonate (—OC(O)OR), carbamate (—OC(O)NHR), ether (—OR), amide (—C(O)NHR), imine (—C=NR), or phosphate (—P(O)(OH)$_2$), where R is alkyl, among others.

In other embodiments, the oxygen atom of one or both OH groups is substituted with an acyl. In further embodiments, the oxygen atom of one or more OH group is substituted with an acyl such as —C(O)C$_{1-6}$alkyl, —C(O)—C$_{1-6}$alk-C$_{3-8}$cycloalkyl, or —C(O)aryl. In still other embodiments, the oxygen atom of one OH group is substituted with —C(O)C$_{1-6}$alkyl, such as —C(O)methyl, —C(O)ethyl, —C(O)propyl, —C(O)butyl, —C(O)pentyl, or —C(O)hexyl. In yet further embodiments, the oxygen atom of one OH group is substituted with —C(O)—C$_{1-6}$alk-C$_{3-8}$cycloalkyl, such as —C(O)CH$_2$CH$_2$(cyclopentyl). In other embodiments, the oxygen atom of one OH group is substituted with —C(O)aryl such as —C(O)(phenyl). Preferably, the estradiol prodrug is estradiol benzoate, estradiol cypionate, estradiol valerate, or estradiol acetate:

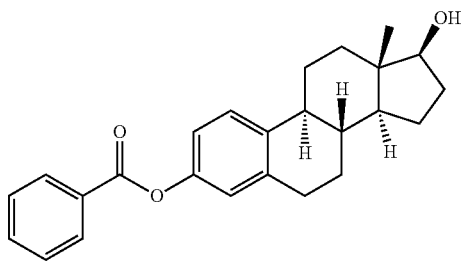

estradiol benzoate

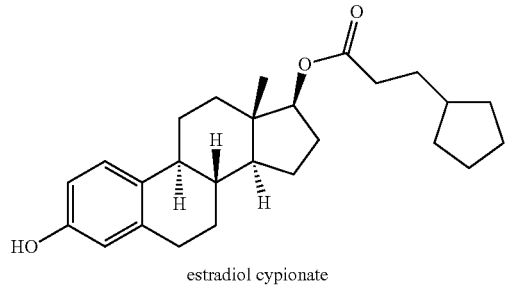

estradiol cypionate

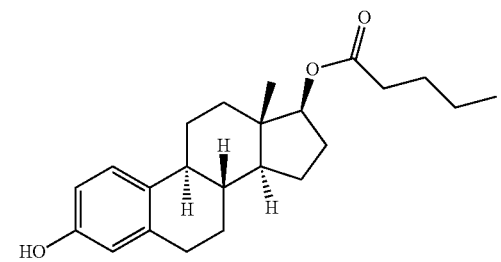

estradiol valerate

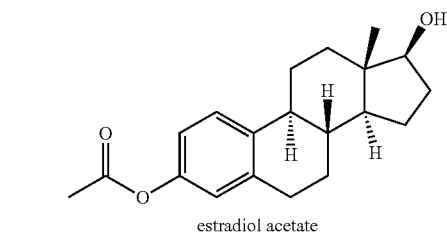

estradiol acetate

The estradiol prodrug may also include compounds having the following general estradiol backbone and optionally having one or two points of unsaturation. The estradiol prodrug also is optionally substituted. In some embodiments, one or more available carbon atom of the following general estradiol backbone is substituted with a moiety aside from hydrogen. In further embodiments, the carbon atom at the 1-, 2-, 4-, 6-, 7-, 8-, 9-, 11-, 12-, 14-, 15-, 16-, or 17-position is substituted. In other embodiments, the carbon atom at the 1-, 2-, 4-, 6-, 7-, 11-, 12-, 15-, 16-, or 17-position is substituted. In yet further embodiments, the carbon atom at the 17-position is substituted. In still other embodiments, the carbon atom at the 10-position is substituted. In further embodiments, one or more available carbon atom is substituted with a methyl group.

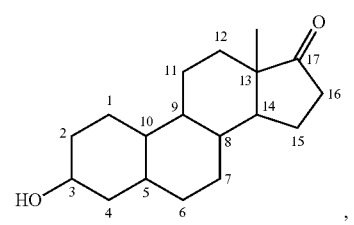

,

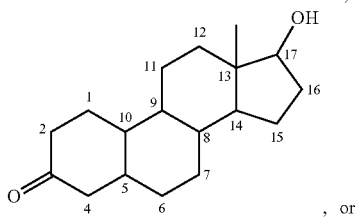

, or

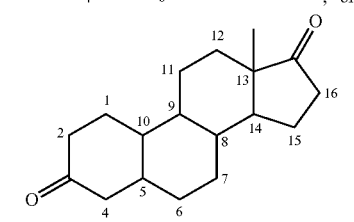

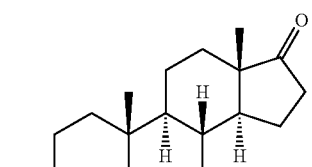

4-androstenedione

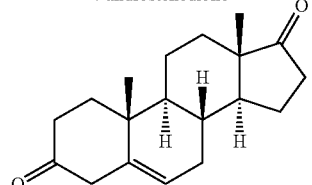

5-androstenedione

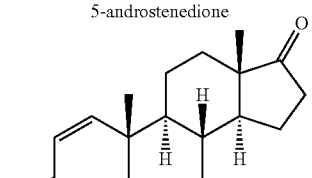

1-androstenedione

In some embodiments, the estradiol prodrug contains a point of unsaturation at C1-C2, C4-C5, or C5-C6. In further embodiments, the estradiol prodrug contains a point of unsaturation at C1-C2. In other embodiments, the estradiol prodrug contains a point of unsaturation at C4-C5. In yet further embodiments, the estradiol prodrug contains a point of unsaturation at C5-C6. Exemplary estradiol prodrugs include dehydroepiandrosterone (DHEA), testosterone, and testosterone derivatives such as testosterone buciclate, androstanedione, androstenedione, androstanediol, androstenediol, androstanolone, or androsteolone.

In some embodiments, the estradiol prodrug is androstenedione such as 5α-androstanedione and 5β-androstanedione.

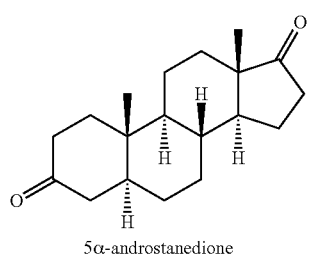

5α-androstanedione

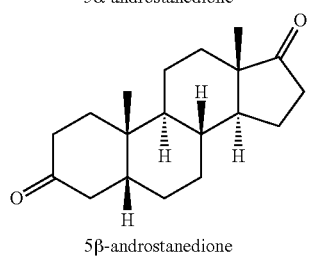

5β-androstanedione

In other embodiments, the estradiol prodrug is androstenedione such as 4-androstenedione, 5-androstenedione, and 1-androstenedione.

In further embodiments, the estradiol prodrug is androstanediol such as 3α,5α-androstanediol, 3β,5α-androstanediol, 3α,5β-androstanediol, or 3β,5β-androstanediol.

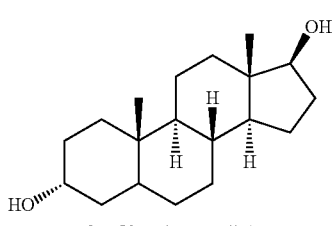

3α, 5β-androstanediol

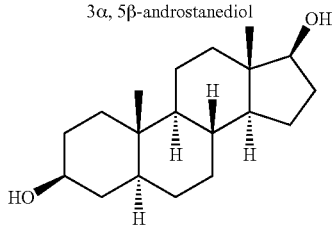

3β, 5α-androstanediol

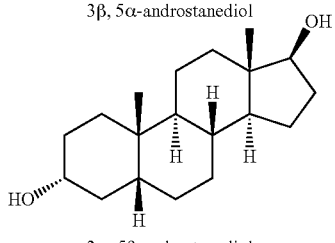

3α, 5β-androstanediol

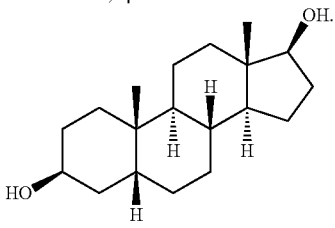

3β, 5β-androstanediol

In yet other embodiments, the estradiol prodrug is androstenediol such as 5-androstenediol, 4-androstenediol, and 1-androstenediol.

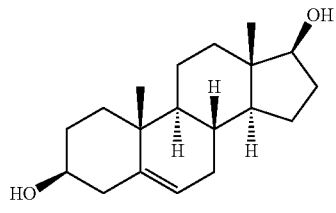
5-androstenediol

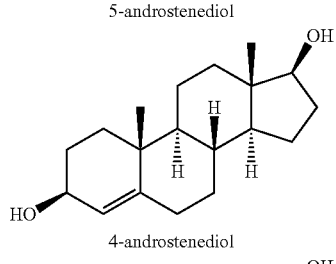
4-androstenediol

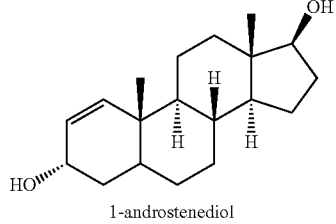
1-androstenediol

In still further embodiments, the estradiol prodrug is androstanolone such as androsterone, epiandrosteron, etiocholanolone, and epietiocholanolone.

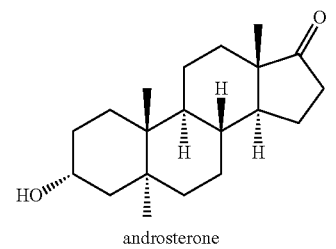
androsterone

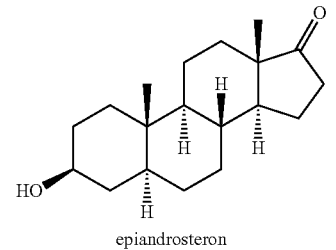
epiandrosteron

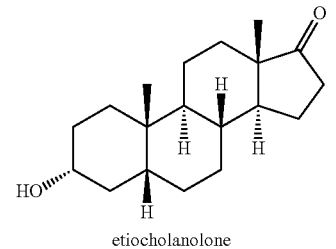
etiocholanolone

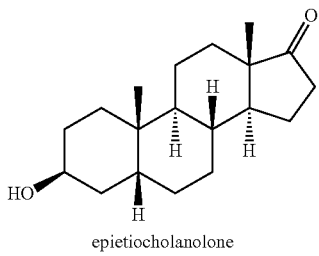
epietiocholanolone

In other embodiments, the estradiol prodrug is androstenolone such as testosterone, epitestosterone, dehydroepiandrosterone, 1-testosterone, 4-dehydroepiandrosterone, and 1-androsterone. In further embodiments, the estradiol prodrug is not dihydrotestosterone.

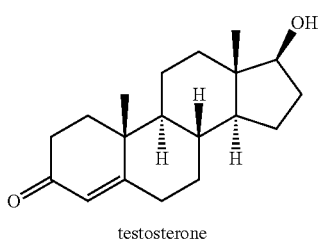
testosterone

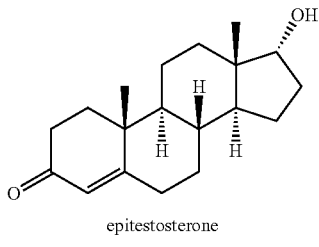
epitestosterone

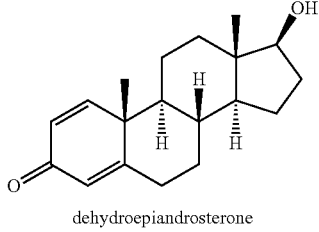
dehydroepiandrosterone

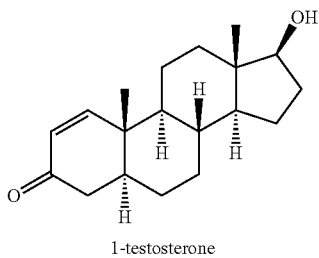
1-testosterone

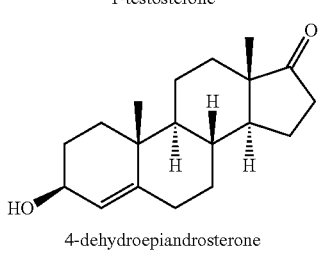
4-dehydroepiandrosterone

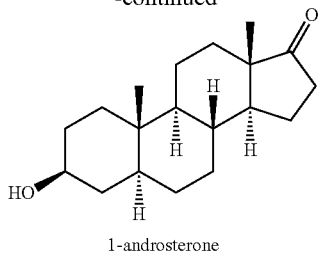

1-androsterone

Estradiols, estradiol derivatives, and estradiol prodrugs optionally can be administered with any of the compounds typically used to improve the safety and efficacy of such compounds, including but not limited to progestins such as desogestrel, drospirenone, ethynodiol, etogestrel, gestodene, levonorgesterel, medroxyprogesterone acetate, megestrol acetate, norethindrone, norethindrone acetate, norgestimate, norgestrel, or progesterone and androgens such as methyltestosterone.

As used herein, the term "isoflavone" refers to a type of often naturally occurring isoflavonoids, such as those a compound having the following general backbone:

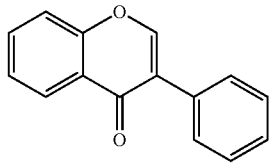 [SMILES: O=c1c(-c2ccccc2)coc2ccccc12]

In some embodiments, the isoflavone is genistein, glycitein biochanin A, daidzein, daidzin, formononetin, equol, irilone, luteone, prunetin, pratensein, glycitien, or a combination of the foregoing. In other embodiments, the isoflavone is a glycoside derivative.

As used herein, the phrase "nonsteroidal anti-inflammatory drug" or "NSAID" refers to a class of drugs that provide analgesic (pain-killing), antipyretic (fever-reducing) effects, or anti-inflammatory effects to a patient. In some embodiments, the NSAID is aspirin, ibuprofen, naproxen, celecoxib, diclofenac, diflunisal, etodolac, indomethacin, ketoprofen, ketorolac, nabumetone, oxaprozin, piroxicam, salsalate, sulindac, and tolmetin. In other embodiments, the NSAID is aspirin, ibuprofen, or naproxen.

While preferred administered amounts of a cholic acid agent, an estradiol, or an isoflavone, or a pharmaceutically acceptable salt thereof, have been described herein, one skilled in the art will understand that the amount of a cholic acid agent, an estradiol, or an isoflavone, or a pharmaceutically acceptable salt thereof, effective to treat dementia and/or the symptoms of dementia can also be determined by one skilled in the art. In general, a typical daily dose of the cholic acid agent or pharmaceutically acceptable salt thereof, is in the range of from about 0.01 mg/kg to about 20 mg/kg. This dose may be administered as a single unit dose or as several separate unit doses. In general, a typical daily dose of the estradiol or pharmaceutically acceptable salt thereof, is in the range of from about 0.01 mg to about 2 mg. This dose may be administered as a single unit dose or as several separate unit doses. In general, a typical daily dose of the isoflavone or pharmaceutically acceptable salt thereof, is in the range of from about 0.01 mg/kg to about 1 g/kg. This dose may be administered as a single unit dose or as several separate unit doses.

The administration of the cholic acid agent, estradiol, or isoflavone can, independently, be through various routes, including orally, nasally, subcutaneously, intravenously, intramuscularly, transdermally, vaginally, rectally, or in any combination thereof.

In some embodiments, the cholic acid agent, estradiol, and isoflavone, or pharmaceutically acceptable salts thereof, are administered concurrently. In other embodiments, the cholic acid agent and estradiol, or a pharmaceutically acceptable salts thereof, are administered concurrently. In further embodiments, the cholic acid agent and isoflavone, or pharmaceutically acceptable salts thereof, are administered concurrently. In yet other embodiments, the estradiol and isoflavone, or pharmaceutically acceptable salts thereof, are administered concurrently. In still further embodiments, the cholic acid agent, estradiol, and isoflavone, or pharmaceutically acceptable salts thereof, are administered sequentially. In other embodiments, the cholic acid agent, isoflavone and, or pharmaceutically acceptable salts thereof, are administered sequentially. In still further embodiments, the estradiol, cholic acid agent, and isoflavone, or pharmaceutically acceptable salts thereof, are administered sequentially. In still other embodiments, the estradiol, isoflavone, and cholic acid agent, or pharmaceutically acceptable salts thereof, are administered sequentially. In further embodiments, the isoflavone, estradiol, and cholic acid agent, or pharmaceutically acceptable salts thereof, are administered sequentially. In yet other embodiments, the isoflavone, cholic acid agent, and isoflavone, or pharmaceutically acceptable salts thereof, are administered sequentially.

The cholic acid agent, estradiol, isoflavone, or a pharmaceutically acceptable salt, or ay combinations of the foregoing, can be administered during a cycle consisting daily dosing for 30 days as a single cycle. In other aspects, the cholic acid agent, estradiol, isoflavone, or a pharmaceutically acceptable salt, or ay combinations of the foregoing, may be administered in divided doses.

According to the described methods, the patient's dementia progression and/or symptoms are assessed. This assessment can occur prior to initiating treatment with the cholic acid agent, an estradiol, or an isoflavone, or a pharmaceutically acceptable salt thereof, or any combinations of the foregoing. This assessment can alternatively or also occur during the course of the treatment period with the cholic acid agent, an estradiol, or an isoflavone, or a pharmaceutically acceptable salt thereof, or any combinations of the foregoing.

Also included within the scope of the disclosure are kits useful for practicing the described methods. The kits comprise at least one cholic acid agent, estradiol, or isoflavone, or a pharmaceutically acceptable salt thereof; together with packaging and instructions for using the kit to treat dementia. In some embodiments, the kits comprise a cholic acid agent, an estradiol, and isoflavone, or a pharmaceutically acceptable salt thereof; together with packaging and instructions for using the kit to treat dementia. In other embodiments, the kits comprise a cholic acid agent and estradiol, or a pharmaceutically acceptable salt thereof, together with packaging and instructions for using the kit to treat dementia. In further embodiments, the kits comprise a cholic acid agent and isoflavone, or a pharmaceutically acceptable salt thereof, together with packaging and instructions for using the kit to treat dementia. In yet other embodiments, the kits comprise an estradiol or isoflavone, or a pharmaceutically acceptable salt thereof, together with packaging and instructions for using the kit to treat dementia.

The disclosure is also directed to pharmaceutical compositions for use in the described methods. These compositions include at least one cholic acid agent, estradiol, or isoflavone, or a pharmaceutically acceptable salt thereof. In some embodiments, these compositions also contain a pharmaceutically acceptable excipient. In some aspects, the pharmaceutical compositions for use in the described methods comprise cholic acid agent, estradiol, and isoflavone, or a pharmaceutically acceptable salt thereof. In other aspects, the pharmaceutical compositions for use in the described methods comprise a cholic acid agent, an estradiol, and a pharmaceutically acceptable excipient. In other aspects, the pharmaceutical compositions for use in the described methods comprise a cholic acid agent, an isoflavone and a pharmaceutically acceptable excipient. In still other aspects, the pharmaceutical compositions for use in the described methods comprise estradiol and isoflavone, and a pharmaceutically acceptable excipient. In further aspects, the pharmaceutical compositions for use in the described methods comprise a cholic acid agent and a pharmaceutically acceptable excipient. In other aspects, the pharmaceutical compositions for use in the described methods comprise an estradiol and a pharmaceutically acceptable excipient. In still further aspects, the pharmaceutical compositions for use in the described methods comprise an isoflavone and a pharmaceutically acceptable excipient. Pharmaceutically acceptable excipient(s) include but are not limited to diluents, lubricants, disintegrants, glidants, and surface-active agents. The pharmaceutical composition described herein may also comprise a non-steroidal anti-inflammatory drug as defined above.

The disclosure is also directed to methods of treating dementia by administering to the patient an effective amount of another pharmaceutical agent for treating dementia or one or more symptoms of dementia. In some embodiments, the another pharmaceutical agent treats Alzheimer's disease, vascular dementia, dementia with lewy bodies, mixed dementia, Parkinson's disease, frontotemporal dementia, Creutzfeldt, Jakob disease, normal pressure hydrocephalus, Huntington's disease, or Wernick Korsakoff syndrome. In other embodiments, the another pharmaceutical agent is a cholinesterase inhibitor, memantine, or ergoloid, or any combinations of the foregoing. In further embodiments, the cholinesterase inhibitor is donepezil, galantamine, or rivastigmine.

In still other aspects, the pharmaceutical compositions for use in the described methods comprise a cholic acid agent, an estradiol or an isoflavone, or a pharmaceutically acceptable salt thereof, or any combinations of the foregoing, and an effective amount of another pharmaceutical agent for use in the treatment of dementia or dementia symptoms. Other embodiments are directed to methods of treating dementia by administering to the patient an effective amount of a cholic acid agent, estradiol, isoflavone, or a pharmaceutically acceptable salt, or ay combinations of the foregoing, and an effective amount of another pharmaceutical agent for use in the treatment of dementia or dementia symptoms. Further embodiments are directed to methods of treating dementia by administering to the patient an effective amount of a cholic acid agent, estradiol, isoflavone, or a pharmaceutically acceptable salt, or ay combinations of the foregoing, and an effective amount of a cholinesterase inhibitor, memantine, or ergoloid, or any combinations of the foregoing.

The following examples are provided to supplement the prior disclosure and to provide a better understanding of the subject matter described herein. These examples should not be considered to limit the described subject matter. It is understood that the examples and embodiments described herein are for illustrative purposes only and that various modifications or changes in light thereof will be apparent to persons skilled in the art and are to be included within, and can be made without departing from, the true scope of the invention.

EXAMPLES

Patients having a diagnosis of dementia are screened and their symptoms assessed. A first subgroup of those patients is administered a treatment regimen that includes cholic acid at dose of 50 mg daily, either as a single dose or as divided doses.

A second subgroup of the patient is administered a treatment regimen that includes 17β-estradiol at dose of 2 mg daily, either as a single dose or as divided doses.

A third subgroup of the patient is administered a treatment regimen that includes daidzein at dose of 50 mg daily, either as a single dose or as divided doses.

For a study period of four weeks, for each subgroup, changes in dementia symptoms are re-assessed following administration of the treatment regimen.

It is to be understood that while the invention has been described in conjunction with the preferred specific embodiments thereof, that the foregoing description and the examples that follow are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains. In addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

What is claimed:

1. A method of treating dementia in a patient, comprising administering to the patient an effective amount of:
   (i) a cholic acid agent or a pharmaceutically acceptable salt thereof,
   (ii) a combination of (i) with an estradiol, an estradiol derivative, or an estradiol prodrug;
   (iii) a combination of (i) with an isoflavone, or
   (iv) a combination of (i) with an isoflavone and an estradiol, an estradiol derivative, or an estradiol prodrug.

2. The method of claim 1, wherein the dementia is Alzheimer's disease, vascular dementia, dementia with lewy bodies, mixed dementia, Parkinson's disease, frontotemporal dementia, Creutzfeldt, Jakob disease, normal pressure hydrocephalus, Huntington's disease, or Wernick Korsakoff syndrome.

3. The method of claim 1, wherein (i), (ii), (iii), or (iv) is administered orally, subcutaneously, intravenously, transdermally, vaginally, rectally or in any combination thereof.

4. The method of claim 1, comprising administering a cholic acid agent.

5. The method of claim 1, wherein the cholic acid agent is ursodeoxycholic acid, cholic acid, chenodeoxycholic acid, tauroursodeoxycholic acid, taurochenodeoxycholic acid, lithocholic acid, taurocholic acid, glycocholic acid, deoxycholic acid, or glycochenodeoxycholic acid, or a pharmaceutically acceptable salt thereof, or a combination of any of the foregoing.

6. The method of claim 1, wherein the effective amount of the cholic acid agent is about 0.01 to about 20 mg/kg/day.

7. The method of claim 1, comprising administering an estradiol.

8. The method of claim 1, wherein the estradiol is 17β-estradiol, estradiol hemihydrate, or a combination of any of the foregoing.

9. The method of claim 1, comprising administering an estradiol derivative.

10. The method of claim 1, wherein the estradiol derivative is an ethinyl estradiol.

11. The method of claim 1, comprising administering an estradiol prodrug.

12. The method of claim 1, wherein the estradiol prodrug is estradiol benzoate, estradiol cypionate, estradiol valerate, estradiol acetate, dehydroepiandrosterone, testosterone, a testosterone derivative, or a combination of any of the foregoing.

13. The method of claim 12, wherein the testosterone derivative is an androstanedione, androstenedione, androstanediol, androstenediol, androstanolone, androstenolone, or a combination of any of the foregoing.

14. The method of claim 1, wherein the effective amount of the estradiol is about 0.01 to about 2 mg/day.

15. The method of claim 1, wherein the isoflavone is genistein, daidzein, glycitein biochanin A, daidzein, daidzin, formononetin, equol, irilone, luteone, prunetin, pratensein, or glycitein.

16. The method of claim 1, wherein the effective amount of the isoflavone is about 0.01 to about 1 g/kg/day.

17. The method of claim 1, further comprising administering to the patient an effective amount of another pharmaceutical agent useful in the treatment of dementia or a symptom of dementia.

18. The method of claim 17, wherein the another pharmaceutical agent is a cholinesterase inhibitor, memantine, ergoloid, or a combination of any of the foregoing or treats Alzheimer's disease, vascular dementia, dementia with lewy bodies, mixed dementia, Parkinson's disease, frontotemporal dementia, Creutzfeldt, Jakob disease, normal pressure hydrocephalus, Huntington's disease, or Wernick Korsakoff syndrome.

19. The method of claim 18, wherein the cholinesterase inhibitor is donepezil, galantamine, rivastigmine, or a combination of any of the foregoing.

20. A pharmaceutical composition comprising:
an effective amount of:
(i) a cholic acid agent, or a pharmaceutically acceptable salt thereof,
(ii) a combination of (i) with an estradiol, an estradiol derivative, or an estradiol prodrug,
(iii) a combination of (i) with an isoflavone, or
(iv) a combination of (i) with an isoflavone and an estradiol, an estradiol derivative, or an estradiol prodrug,
and a pharmaceutically acceptable excipient.

21. The pharmaceutical composition of claim 20, further comprising a non-steroidal anti-inflammatory drug.

22. A method for reducing the likelihood of developing dementia in a patient taking a long-therapy of a non-steroidal anti-inflammatory drug or aspirin, comprising administering to the patient an effective amount of:
(i) a cholic acid agent or a pharmaceutically acceptable salt thereof,
(ii) a combination of (i) with estradiol, an estradiol derivative, or an estradiol prodrug,
(iii) a combination of (i) with an isoflavone, or
(iv) a combination of (i) with an isoflavone and an estradiol, an estradiol derivative, or an estradiol prodrug.

23. The method of claim 5, wherein the cholic acid agent is tauroursodeoxycholic acid.

* * * * *